(12) United States Patent
Petrov et al.

(10) Patent No.: US 7,420,094 B2
(45) Date of Patent: Sep. 2, 2008

(54) CATALYTIC ISOMERIZATION PROCESSES OF 1,3,3,3-TETRAFLUOROPROPENE FOR MAKING 2,3,3,3-TETRAFLUOROPROPENE

(75) Inventors: Viacheslav A. Petrov, Hockessin, DE (US); Mario Joseph Nappa, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/897,582

(22) Filed: Aug. 31, 2007

(65) Prior Publication Data

US 2008/0058562 A1 Mar. 6, 2008

Related U.S. Application Data

(60) Provisional application No. 60/842,449, filed on Sep. 5, 2006.

(51) Int. Cl.
*C07C 17/00* (2006.01)
*C07C 29/08* (2006.01)

(52) U.S. Cl. .................. 570/151; 570/123; 570/168
(58) Field of Classification Search ............... 570/123, 570/151, 168
See application file for complete search history.

(56) References Cited

U.S. PATENT DOCUMENTS

| | | | |
|---|---|---|---|
| 2,996,665 | A | 8/1961 | Rausch |
| 5,036,036 | A | 7/1991 | Lerou |
| 2006/0106263 | A1 | 5/2006 | Miller et al. |
| 2007/0100173 | A1 | 5/2007 | Miller et al. |
| 2007/0100175 | A1 | 5/2007 | Miller et al. |

FOREIGN PATENT DOCUMENTS

| WO | WO 2005/108334 A1 | 11/2005 |
|---|---|---|
| WO | PCT/US2007/014645 | 6/2007 |

*Primary Examiner*—Sikarl A Witherspoon

(57) ABSTRACT

The present invention relates to a process of catalyzed isomerization of HFC-1234ze to make HFC-1234yf. The process comprises contacting HFC-1234ze with a suitable catalyst in a reactor to obtain a product mixture comprising HFC-1234yf.

13 Claims, No Drawings

CATALYTIC ISOMERIZATION PROCESSES OF 1,3,3,3-TETRAFLUOROPROPENE FOR MAKING 2,3,3,3-TETRAFLUOROPROPENE

BACKGROUND OF THE INVENTION

1. Field of the Disclosure

The present disclosure relates in general to the processes of catalyzed isomerization of 1,3,3,3-tetrafluoropropene (HFC-1234ze) to make 2,3,3,3-tetrafluoropropene (HFC-1234yf).

2. Description of Related Art

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

Tetrafluoropropenes, having zero ozone depletion and low global warming potential, have been identified as potential refrigerants. However, the toxicity, boiling point, and other physical properties in this class of chemicals varies greatly from isomer to isomer. One tetrafluoropropenes having valuable properties is 2,3,3,3 tetrafluoropropene (HFC-1234ye). Thus, there is a need for new manufacturing processes for the production of tetrafluoropropenes.

SUMMARY OF THE INVENTION

The present disclosure provides a process of catalyzed isomerization of HFC-1234ze to make HFC-1234yf. The process comprises contacting HFC-1234ze with a suitable catalyst in a reactor to obtain a product mixture comprising HFC-1234yf.

The present disclosure is to a new manufacturing process for the production of 2,3,3,3-tetrafluoropropene. The process includes the step of contacting 1,3,3,3-tetrafluoropropene with a catalyst in a reactor to obtain a product mixture comprising 2,3,3,3-tetrafluoropropene The foregoing general description and the following detailed description are exemplary and explanatory only and are not restrictive of the invention, as defined in the appended claims.

DETAILED DESCRIPTION OF THE INVENTION

Before addressing details of embodiments described below, some terms are defined or clarified.

HFC-1234ze may exist as one of two configurational isomers, E or Z. HFC-1234ze as used herein refers to the isomers, E-HFC-1234ze or Z-HFC-1234ze, as well as any combinations or mixtures of such isomers.

The term "a chromium oxyfluoride catalyst" is intended to mean a chromium oxyfluoride represented by formula $Cr_2O_xF_y$ wherein $x+y/2=3$.

The term "amorphous" is intended to mean that there is no substantial peak in a X-ray diffraction pattern of the subject solid.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

A process has been provided to catalytically isomerize HFC-1234ze to form HFC-1234yf. The process comprises contacting HFC-1234ze with a suitable catalyst in a reactor to obtain a product mixture comprising HFC-1234yf.

In one embodiment of this invention, the suitable catalyst contains chromium. Such suitable catalysts include chromium oxyfluoride.

Many aspects and embodiments have been described in this disclosure and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

The synthesis of HFC-1234ze is disclosed by Mukhopadhyay et al. in US Patent Publication Number 2005/0245773 A1, which is incorporated herein by reference.

The chromium oxyfluoride catalysts can be made by treating $Cr_2O_3$ (chromium oxide) with a source of fluorine such as HF, $CCl_3F$ or hydrofluorocarbons. In one embodiment of this invention, a chromium oxyfluoride catalyst is made by treating dry $Cr_2O_3$ with a fluorination agent such as $CCl_3F$ or HF. This treatment can be accomplished by placing the $Cr_2O_3$ in a suitable container (which can be the reactor to be used to perform the dehydrofluorination reaction) and thereafter passing HF over the dry $Cr_2O_3$ for a suitable period of time (e.g., about 15 to 300 minutes) at a suitable temperature (e.g., about 200° C. to 450° C.), such as what described in Example 1.

In another embodiment of this invention, a chromium oxyfluoride catalyst is made by treating $Cr_2O_3$ with a hydrofluorocarbon at an elevated temperature.

In another embodiment of this invention, a chromium oxyfluoride catalyst is made in situ. For example, the reactant HFC-E-1234ze can be employed in the formation of a chromium oxyfluoride catalyst by heating together with $Cr_2O_3$ in the reactor.

$Cr_2O_3$ is commercially available from Engelhard Corporation (101 Wood Avenue, P.O. Box 770, Iselin, N.J. 08830-0770).

$Cr_2O_3$ can also be prepared by pyrolysis of ammonium dichromate as disclosed in U.S. Pat. No. 5,036,036, which is incorporated herein by reference.

$Cr_2O_3$ can also be prepared by the reaction of chromium (VI) oxide with a reducing solvent, such as methanol, as disclosed in U.S. Pat. No. 4,828,818, which is incorporated herein by reference.

$Cr_2O_3$ can also be prepared by reducing chromium (VI) oxide in water with a suitable reducing agent, such as ethanol, as disclosed in U.S. Pat. No. 3,258,500, which is incorporated herein by reference.

The amount of potassium and other alkali metals in $Cr_2O_3$ can be reduced by a water washing step as disclosed in U.S. Pat. No. 5,036,036.

In one embodiment of this invention, the chromium oxyfluoride catalyst has surface areas of about 20 $m^2/g$ to about 500 $m^2/g$.

In another embodiment of this invention, the chromium oxyfluoride catalyst has surface areas of about 40 $m^2/g$ to about 350 $m^2/g$.

In another embodiment of this invention, the chromium oxyfluoride catalyst has surface areas of about 60 $m^2/g$ to about 300 $m^2/g$.

In another embodiment of this invention, the chromium oxyfluoride catalyst has surface areas of about 100 $m^2/g$ to about 300 $m^2/g$.

In one embodiment of this invention, the chromium oxyfluoride catalyst contains an alkali metal content of about 2000 ppm or less.

In another embodiment of this invention, the chromium oxyfluoride catalyst contains an alkali metal content of about 300 ppm or less.

In another embodiment of this invention, the chromium oxyfluoride catalyst contains an alkali metal content of about 100 ppm or less.

In one embodiment of this invention, the chromium oxyfluoride catalyst is amorphous.

In another embodiment of this invention, the chromium oxyfluoride catalyst is prepared from crystalline $\alpha$-$Cr_2O_3$.

In another embodiment of this invention, suitable catalysts include transition metal modified chromium oxides and transition metal modified chromium oxyfluorides. Such transition metals include magnesium (e.g. magnesium fluoride), Group VIIB metals (e.g., manganese), Group IIIB metals (e.g., lanthanum), and zinc. In use, such transition metals are normally present as halides (e.g., fluorides), as oxides and/or as oxyhalides. Typically, these transition metals are supported on chromium oxides or chromium oxyfluorides.

In another embodiment of this invention, other suitable catalysts which may be used for the isomerization contain aluminum. Such catalysts include fluorided alumina, aluminum fluoride. Such catalysts also include transition metal modified alumina, transition metal modified fluorided alumina and transition metal modified aluminum fluoride. Such transition metals include magnesium (e.g. magnesium fluoride), Group VIIB metals (e.g., manganese), Group IIIB metals (e.g., lanthanum), and zinc. In use, such transition metals are normally present as halides (e.g., fluorides), as oxides and/or as oxyhalides. Typically, these transition metals are supported on alumina, fluorided alumina or aluminum fluoride. Fluorided alumina and aluminum fluoride can be prepared as described in U.S. Pat. No. 4,902,838, herein incorporated by reference.

The contact time of HFC-1234ze with the chromium oxyfluoride catalyst can vary widely depending on the degree of conversion desired and generally will be from about 1 second to about 1000 seconds. In one embodiment of the invention, the contact time ranges from about 10 seconds to about 200 seconds.

The temperature employed in the isomerization processes typically ranges from about 200° C. to 500° C. In one embodiment of the invention, the temperature employed in the isomerization processes ranges from about 300° C. to 400° C.

The reaction pressure for the processes above can be subatmospheric, atmospheric or superatmospheric. In one embodiment of the invention, the reaction pressure is near atmospheric.

Optionally, the reactions in the processes above can be done in the presence of oxygen. In one embodiment of the invention, the reactions in the processes above is done in the presence of air. In another embodiment of the invention, air is co-fed with the reactant into the reactor.

Optionally, the reactions in the processes above can be done in the presence of inert gases such as nitrogen, helium, argon, or their mixtures thereof. In one embodiment of the invention, the inert gas is co-fed with the reactant into the reactor. In another embodiment of the invention, the inert gas is nitrogen.

In one embodiment of this invention, HFC-1234yf present in the product mixture may be separated from the other components of the product mixture and unreacted starting materials by fractional distillation.

In another embodiment of this invention, HF is added to the product mixture, and separation of HFC-1234yf includes isolation of azeotrope or near azeotrope of HFC-1234yf and HF and further processing to produce HF-free HFC-1234yf by using procedures similar to that disclosed in US Patent Publication US 2006/0106263 A1, herein incorporated by reference.

U.S. Application No. 60/732,321, filed on Nov. 1, 2005 and incorporated herein by reference, discloses an azeotrope or near-azeotrope composition of HFC-1234yf and HF.

Unreacted HFC-1234ze can be separated and recycled to the reactor for the production of additional HFC-1234yf.

In one embodiment of this invention, unreacted HFC-1234ze present in the product mixture may be separated from the other components of the product mixture by fractional distillation.

In another embodiment of this invention, HF is added to the product mixture, and separation of unreacted HFC-1234ze includes isolation of azeotrope or near azeotrope of HFC-1234ze and HF and further processing to produce HF-free HFC-1234ze by using procedures similar to that disclosed in US Patent Publication US 2006/0106263 A1.

U.S. Application No. 60/732,397, filed on Nov. 1, 2005 and incorporated herein by reference, discloses an azeotrope or near-azeotrope composition of the E-isomer of HFC-1234ze and HF. U.S. Application No. 60/816,650, filed on Jun. 27, 2006 and incorporated herein by reference, discloses an azeotrope or near-azeotrope composition of the Z-isomer of HFC-1234ze and HF.

The reactors, distillation columns, and their associated feed lines, effluent lines, and associated units used in applying the processes of embodiments of this invention should be constructed of materials resistant to corrosion. Typical materials of construction include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

EXAMPLES

The concepts described herein will be further described in the following examples, which do not limit the scope of the invention described in the claims.

Legend

1234ze is $CF_3CH=CHF$  1234yf is $CF_3CF=CH_2$

Example 1

Chromium oxide used in this example was synthesized according to the process described in U.S. Pat. No. 3,258,500 from the reduction of chromium trioxide. This form of chromium oxide is usually amorphous and has a surface area in excess of 180 $m^2/gm$.

An Inconel tube (⅝ inch OD) was filled with 6 cc (7.12 gm) of chromium oxide gel pellets, crushed and sieved to 12/20 mesh. The catalyst was heated to 200° C. for 15 minutes under a purge of $N_2$ (50 sccm, $8.33\times10^{-7}$ $m^3/s$). Then the temperature was raised to 325° C. for 10 minutes, to 400° C. for 20 minutes, and lowered to 300° C. for 35 minutes. The temperature was raised to 325° C. for 60 minutes while flowing $N_2$ (35 sccm, $5.83\times10^{-7}$ $m^3/s$) and HF (12 sccm, $2.00\times10^{-7}$ $m^3/s$) for 35 minutes. While maintaining this flow, the temperature was raised to 350° C. for 60 minutes, 375° C. for 90 minutes, 400° C. for 30 minutes, and 425° C. for 40 minutes. The flow of $N_2$ was reduced to 25 sccm ($4.17\times10^{-7}$ $m^3/s$) and HF raised to 20 sccm ($3.33\times10^{-7}$ $m^3/s$) for 20 minutes. Then the flow of $N_2$ was reduced to 15 sccm ($2.50\times10^{-7}$ $m^3/s$) and HF raised to 28 sccm ($4.67\times10^{-7}$ $m^3/s$) for 20 minutes. Then the flow of $N_2$ was reduced to 5 sccm ($8.33\times10^{-8}$ $m^3/s$) and HF raised to 36 sccm ($6.00\times10^{-7}$ $m^3/s$) for 20 minutes. Finally, the $N_2$ was shut off and the HF flow was raised to 40 sccm ($6.67\times10^{-7}$ $m^3/s$) for 20 minutes and then the temperature was reduced to the reaction temperature.

The temperature of the catalyst bed was set to 350° C. and E-HFC-1234ze (E-1,3,3,3-tetrafluoropropene) was flowed through the reactor at 6 sccm ($1.00\times10^{-7}$ $m^3/s$). The product mixture effluent was analyzed by both GC-MS and NMR and found to have the following composition: (analytical results were given in units of GC area %) 31.1% Z-HFC-1234ze, 59.9% E-HFC-1234ze, 1.3% 236fa, 3.8% 245fa, and 3.9% HFC-1234yf.

Example 2

This example is prophetic. All the other conditions are the same as in Example 1. The temperature of the catalyst bed is set to 400° C. and E-HFC-1234ze is flowed through the reactor at 6 sccm ($1.00\times10^{-7}$ $m^3/s$). The product mixture effluent is analyzed by both GC-MS and NMR and found to have the following composition: (analytical results were given in units of GC area %) 35% Z-HFC-1234ze, 40% E-HFC-1234ze, 2% 236fa, 5% 245fa, and 18% HFC-1234yf.

Example 3

This example is prophetic. All the other conditions are the same as in Example 1.

The temperature of the catalyst bed is set to 350° C. and E-HFC-1234ze is flowed through the reactor at 3 sccm ($2.00\times10^{-8}$ $m^3/s$), thereby doubling the contact time compared to Example 1. The product mixture effluent is analyzed by both GC-MS and NMR and found to have the following composition: (analytical results were given in units of GC area %) 37% Z-HFC-1234ze, 35% E-HFC-1234ze, 3% 236fa, 5% 245fa, and 20% HFC-1234yf.

Example 4

This example is prophetic. In this example, a catalyst of higher surface area is used as described in U.S. Pat. No. 4,828,818. This is an aerogel catalyst with a high surface area, typically greater than 400 $m^2/gm$. An inconel tube (⅝ inch OD) is filled with 6 cc (0.38 gm) of chromium oxide gel particles, crushed and sieved to 12/20 mesh. The catalyst is heated to 200° C. for 15 minutes under a purge of $N_2$ (50 sccm, $8.33\times10^{-7}$ $m^3/s$). Then the temperature is raised to 325° C. for 10 minutes, to 400° C. for 20 minutes, and lowered to 300° C. for 35 minutes. The temperature is raised to 325° C. for 60 minutes while flowing $N_2$ (35 sccm, $5.83\times10^{-7}$ $m^3/s$) and HF (12 sccm, $2.00\times10^{-7}$ $m^3/s$) for 35 minutes. While maintaining this flow, the temperature is raised to 350° C. for 60 minutes, 375° C. for 90 minutes, 400° C. for 30 minutes, and 425° C. for 40 minutes. The flow of $N_2$ is reduced to 25 sccm ($4.17\times10^{-7}$ $m^3/s$) and HF raised to 20 sccm ($3.33\times10^{-7}$ $m^3/s$) for 20 minutes. Then the flow of $N_2$ is reduced to 15 sccm ($2.50\times10^{-7}$ $m^3/s$) and HF raised to 28 sccm ($4.67\times10^{-7}$ $m^3/s$) for 20 minutes. Then the flow of $N_2$ is reduced to 5 sccm ($8.33\times10^{-8}$ $m^3/s$) and HF raised to 36 sccm ($6.00\times10^{-7}$ $m^3/s$) for 20 minutes. Finally, the $N_2$ is shut off and the HF flow is raised to 40 sccm ($6.67\times10^{-7}$ $m^3/s$) for 20 minutes and then the temperature is reduced to the reaction temperature.

The temperature of the catalyst bed is set to 350° C. and E-HFC-1234ze is flowed through the reactor at 6 sccm ($1.00\times10^{-7}$ $m^3/s$). The product mixture effluent is analyzed by both GC-MS and NMR and found to have the following composition: (analytical results were given in units of GC area %) 30% E-HFC-1234ze, 30% E-HFC-1234ze, 1.3% 236fa, 4.8% 245fa, and 33.9% HFC-1234yf. The higher surface area catalyst substantially increases the amount of the desired HFC-1234yf.

What is claimed is:

1. A process comprising: contacting 1,3,3,3-tetrafluoropropene with a catalyst in a reactor to obtain a product mixture comprising 2,3,3,3-tetrafluoropropene.

2. The process of claim 1 wherein the catalyst contains chromium.

3. The process of claim 2 wherein the catalyst is a chromium oxyfluoride.

4. The process of claim 3 wherein said chromium oxyfluoride is made by reacting $Cr_2O_3$ with a source of fluorine.

5. The process of claim 4 wherein said source of fluorine is selected from the group consisting of HF, $CCl_3F$ and hydrofluorocarbons.

6. The process of claim 2 wherein said catalyst is a transition metal modified chromium oxide or a transition metal modified chromium oxyfluoride.

7. The process of claim 6 wherein said transition metal is selected from the group consisting of magnesium, Group VIIB metals, Group IIIB metals, and zinc.

8. The process of claim 7 wherein said transition metal is supported on chromium oxide or chromium oxyfluoride.

9. The process of claim 1 wherein catalyst contains aluminum.

10. The process of claim 9 wherein said catalyst is fluorided alumina or aluminum fluoride.

11. The process of claim 9 wherein said catalyst is selected from the group consisting of transition metal modified alumina, transition metal modified fluorided alumina and transition metal modified aluminum fluoride.

12. The process of claim 11 wherein said transition metal is selected from the group consisting of magnesium, Group VIIB metals, Group IIIB metals, and zinc.

13. The process of claim 12 wherein said transition metal is supported on alumina, fluorided alumina or aluminum fluoride.

* * * * *